United States Patent [19]
Hutt et al.

[11] Patent Number: 5,639,918
[45] Date of Patent: Jun. 17, 1997

[54] INTERMEDIATE COMPOUNDS USEFUL IN THE PREPARATION OF FUNGICIDAL COMPOSITIONS CONTAINING (BENZYLIDENE)-AZOLYLMETHYCLYCLOALKANE

[75] Inventors: Jean Hutt, Lyons; Jacques Mugnier, Sillingy; Alfred Greiner, St Cyr Au Mont D'or; Regis Pepin, Rilleux La Pape, all of France

[73] Assignee: Rhone-Poulenc Agrochimie, Lyons, France

[21] Appl. No.: 312,475

[22] Filed: Sep. 26, 1994

Related U.S. Application Data

[62] Division of Ser. No. 20,225, Feb. 16, 1995, Pat. No. 5,380,743, which is a continuation of Ser. No. 458,222, Dec. 28, 1989, abandoned.

[30] Foreign Application Priority Data

Dec. 29, 1988 [FR] France ............... 88 17580
Jun. 30, 1989 [FR] France ............... 89 09079
Jul. 13, 1989 [FR] France ............... 89 09741

[51] Int. Cl.⁶ .............. C07C 49/23; C07C 49/237; C07C 49/252; C07C 49/798
[52] U.S. Cl. .............. 568/329; 549/332; 568/330
[58] Field of Search .............. 568/329, 330; 549/332

[56] References Cited

U.S. PATENT DOCUMENTS

| | | | |
|---|---|---|---|
| 2,465,855 | 5/1949 | Dorman et al. | 568/329 X |
| 3,288,862 | 11/1966 | Dowbenko | 568/330 X |
| 3,468,881 | 9/1969 | Szmuszkovicz | 568/330 X |
| 3,857,953 | 12/1974 | Scanlon | 424/331 |
| 4,328,348 | 5/1982 | Ogata et al. | 548/335 |
| 4,503,062 | 3/1985 | Gravestock | 514/383 |
| 4,711,895 | 12/1987 | Hazato et al. | 514/530 |
| 4,863,505 | 9/1989 | Kumazawa et al. | 548/262.2 |
| 4,904,640 | 2/1990 | Markert et al. | 512/8 |
| 4,920,138 | 4/1990 | Ito et al. | 514/383 |
| 5,157,131 | 10/1992 | Chabardes et al. | 549/332 |
| 5,380,743 | 1/1995 | Hutt et al. | 514/391 |

FOREIGN PATENT DOCUMENTS

| | | | |
|---|---|---|---|
| 0057882 | 8/1982 | European Pat. Off. | 568/330 |
| 0267778 | 5/1988 | European Pat. Off. | 514/399 |
| 0272895 | 6/1988 | European Pat. Off. | 514/313 |
| 0294222 | 12/1988 | European Pat. Off. | 514/383 |
| 2245518 | 4/1973 | Germany . | |
| 3630840 | 3/1987 | Germany | 514/383 |
| 4027980 | 3/1992 | Germany | 568/329 |
| 1305025 | 1/1973 | United Kingdom | 514/383 |
| 2180236 | 3/1987 | United Kingdom | 514/383 |

OTHER PUBLICATIONS

Cromwell et al, J. Org. Chem., vol. 33, pp. 1895 to 1913 (1968).
Mukaiyama et al, J. Amer. Chem. Soc., vol. 96, pp. 7503 to 7509 (1974).
J.-M. Conia et al.: "L'isomerisation Des Alcoylidene-2 Cyclohexanones, -Cyclopentanones Et -Cyclobutanones Par l'acide Polyphosphorque," Bulletin De La Societe Chimique De France, Nos. 8–9, 1970, pp. 2972–2980.

P. Perjesi et al.: "Reaction of Cyclic Thioureas with 2-Benzylidenecycloalkanones," Chemische Berichte, vol. 120, No. 8, 1987, pp. 1449–1450.

G. Le Guillanton: "Action Des Agents Epoxydants Sur Les Alkylidene-2 Cyclopentanones," Bulletin De La Societe Chimique De France, No. 8, 1969, pp. 2871–2875.

D. A. Whiting: "Photodimerisation of 2-Benzyl-5-p-Bromobenzylidenecyclopentanone, a Crystal-Crystal Transformation : X-Ray Study of the Dimer," Journal of the Chemical Society (C), vol. 20, 1971, pp. 3396–3398.

*Primary Examiner*—Floyd D. Higel
*Attorney, Agent, or Firm*—Morgan & Finnegan, L.L.P.

[57] ABSTRACT

(Benzylidene)-azolylmethylcycloalkane or -alkene of formula

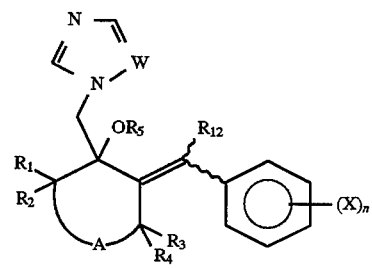

IA

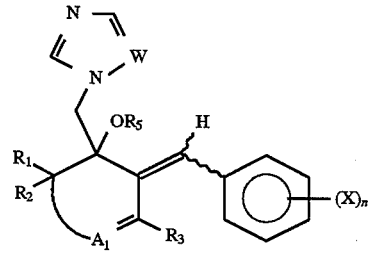

IB in which:

A and $A_1$ are hydrocarbon chains of 1 to 3 carbon atoms, $R_1$, $R_2$, $R_3$, $R_4$ and $R_5$ are hydrocarbon radicals, X is halogen, Y is H or halogen, n=1, 2 or 3, W is —CH= or —N=.

Use as a fungicide.

9 Claims, No Drawings

INTERMEDIATE COMPOUNDS USEFUL IN THE PREPARATION OF FUNGICIDAL COMPOSITIONS CONTAINING (BENZYLIDENE)-AZOLYLMETHYCLYCLOALKANE

The present application is a divisional of U.S. application Ser. No. 08/020,225 filed Feb. 16, 1995, now U.S. Pat. No. 5,380,743, which is a continuation of U.S. application Ser. No. 07/458,222 filed Dec. 28, 1989, now abandoned.

CLAIM OF PRIORITY

This application claims the benefit of the following prior applications: French Ser. No. 8817580 filed on Dec. 29, 1988; French Ser. No. 8909079 filed on Jun. 30, 1989; and French Ser. No. 8909741 filed on Jul. 13, 1989.

The present invention relates to new compounds, for use as plant-protection agents, containing (benzylidene)-azolylmethylcycloalkane or -cycloalkene groups. It also relates to the processes for preparing the said compounds and to the products which are usable, where appropriate, by way of intermediates in the preparation processes. It relates, next, to the use of these compounds by way of fungicides, to the fungicidal compositions based on these compounds and to the processes for controlling fungal diseases of crops using these compounds. It also relates to a product of multiplication of cultivated plants, which has undergone a protective treatment with a compound of the invention.

Many products containing triazole groups, in particular fungicides, are already known. In particular, triazole fungicides containing a tetrahydrofuran ring are known from Patent Applications EP 151,084, 246,982, 121,979 and 89,100. Triazole fungicides containing a cyclopentane ring are known from Patent Applications EP 272,895 and 267,778, DE 3,630,840 and BE 867,245. Triazole fungicides containing a cycloalkane group are known from Patent Application EP 324,646 and U.S. Pat. No. 4,684,396. Triazole fungicides containing a dioxolane ring are known from U.S. Pat. No. 4,160,838.

Thus, in the light of this prior art which, as far as the Applicant is aware, enables the state of the art to be illustrated according to rule 27-1, section C, an object of the present invention is to propose other broad-spectrum fungicidal compounds which are useful, in particular, in the treatment of diseases of the stem base such as eyespot, or of the leaf such as powdery mildew, septoriosis, pyriculariosis, fusarioses or rhynchosporiosis, and diseases caused by pathogenic fungi such as Botrytis, Phoma and Aschochyta in crops as diverse as cereals, vine, rice, maize and soya, for example.

These compounds are of the formulae IA or IB below:

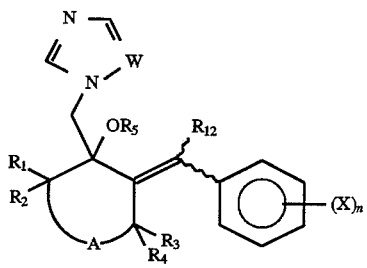

IA

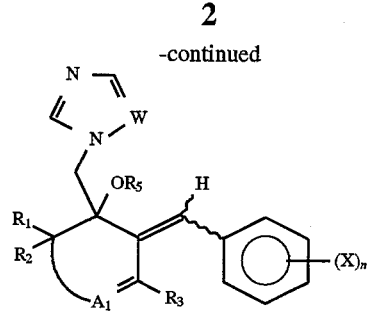

IB in which

A is $-CR_6R_7-$ or $-CR_6R_7CR_8R_9-$ or $-CR_6R_7CR_8R_9CR_{10}R_{11}-$, $A_1$ is $CR_7=$, $-CR_6R_7-CR_9=$ or $-CR_6R_7-CR_8R_9-CR_{11}=$, i.e. the cycloalkane can be a cyclopentane or cyclohexane or cycloheptane or cyclopentene, cyclohexene or cycloheptene, X is a halogen atom, preferably a fluorine, bromine or chlorine atom, or a cyano or nitro group, or a $C_1-C_1$ alkyl or $C_1-C_1$ alkoxy group, optionally halogenated, n is a positive integer or zero, less than 6, it being possible for the groups X to be identical or different when n is greater than 1, W denotes a trivalent group consisting of either a =CH— group or a nitrogen atom =N—, $R_1$ and $R_2$, which may be identical or different, denote a hydrogen atom or a $C_1-C_4$ alkyl radical, optionally substituted (e.g. with one or more atoms or radicals such as halogen atoms and $C_1-C_4$ alkoxy, mono- or polyhalo($C_1-C_4$ alkoxy), $C_2-C_4$ alkenyl, $C_2-C_4$ alkynyl, mono- or polyhalo($C_2-C_4$ alkenyl) and mono- or polyhalo($C_2-C_4$ alkynyl) radicals), $C_1-C_4$ alkoxy radical, optionally substituted (e.g. with one or more atoms or radicals such as halogen atoms and $C_1-C_4$ alkoxy, mono- or polyhalo($C_1-C_4$ alkoxy), $C_2-C_4$ alkenyl, $C_2-C_4$ alkynyl, mono- or polyhalo($C_2-C_4$ alkenyl) and mono- or polyhalo($C_2-C_4$ alkynyl) radicals), or $C_3-C_7$ cycloalkyl, $C_6-C_{10}$ aryl (in particular phenyl) or $C_7-C_{11}$ aralkyl (in particular benzyl) radicals, it being possible for these various radicals to be optionally substituted (e.g. with one or more atoms or radicals such as halogen atoms, $C_1-C_4$ alkyl radicals, mono- or polyhalo($C_1-C_4$ alkyl) radicals, $C_1-C_4$ alkoxy radicals and mono- or polyhalo($C_1-C_4$ alkoxy) radicals), $R_1$ and $R_2$ together can form a $C_2-C_5$ hydrocarbon chain making a ring with the carbon to which $R_1$ and $R_2$ are attached, this chain optionally being substituted as for the $C_6-C_{10}$ aryl radicals mentioned above, or $R_1$ and $R_2$ together can form a $C_2-C_5$ dioxolane hydrocarbon chain with the carbon to which $R_1$ and $R_2$ are attached, this chain optionally being substituted as for the $C_6-C_{10}$ aryl radicals mentioned above.

$R_3$ and $R_6$ to $R_{11}$, which may be identical or different, denote a hydrogen atom or a $C_1-C_4$ alkyl radical, optionally substituted (e.g. with one or more atoms or radicals such as halogen atoms and $C_1-C_4$ alkoxy and mono- or polyhalo($C_1-C_4$ alkoxy) radicals), or $C_3-C_7$ cycloalkyl, $C_5-C_{10}$ aryl (in particular phenyl) or $C_7-C_{11}$ aralkyl (in particular benzyl) radicals, it being possible for these various radicals to be optionally substituted (e.g. with one or more atoms or radicals such as halogen atoms, $C_1-C_4$ alkyl radicals, mono- or polyhalo($C_1-C_4$ alkyl) radicals, $C_1-C_4$ alkoxy radicals and mono- or polyhalo($C_1$-$C_4$ alkoxy) radicals), or alternatively two adjacent radicals of the chain A, together with the atoms of A to which they are attached, form a benzene ring fused to the cycloalkane, denotes a hydrogen atom, a $C_1$-$C_4$ alkyl radical, optionally substituted (e.g. with one or more atoms or radicals such as halogen atoms and $C_1$-$C_4$ alkoxy, mono- or polyhalo($C_1$-$C_4$ alkoxy), $C_2$-$C_4$ alkenyl, $C_2$-$C_4$ alkynyl, mono-or polyhalo($C_2$-$C_4$ alkenyl) and mono- or polyhalo($C_2$-$C_4$ alkynyl) radicals), or $C_3$-$C_7$ cycloalkyl, $C_6$-$C_{10}$ aryl (in particular phenyl) or $C_7$-$C_{11}$ aralkyl (in particular benzyl) radicals, it being possible for these various radicals to be optionally substituted (e.g. with one or more atoms or radicals such as halogen atoms, $C_1$-$C_4$ alkyl radicals, mono- or polyhalo($C_1$-$C_4$ alkyl) radicals, $C_1$-$C_4$ alkoxy radicals and mono- or polyhalo($C_1$-$C_4$ alkoxy) radicals), or $R_5$ denotes a group C(=O)—$R_{13}$, $R_{13}$ denoting a $C_1$-$C_4$ alkyl radical, optionally substituted (e.g. with one or more atoms or radicals such as halogen atoms and $C_1$-$C_4$ alkoxy, mono- or polyhalo($C_1$-$C_4$ alkoxy), $C_2$-$C_4$ alkenyl, $C_2$-$C_4$ alkynyl, mono- or polyhalo ($C_2$-$C_4$ alkenyl) and mono- or polyhalo($C_2$-$C_4$ alkynyl) radicals), or $C_3$-$C_7$ cycloalkyl, $C_5$-$C_{10}$ aryl (in paticular phenyl) or $C_7$-$C_{11}$ aralkyl (in particular benzyl) radicals, it being possible for these various radicals to be optionally substituted (e.g. with one or more atoms or radicals such as halogen atoms, $C_1$-$C_4$ alkyl radicals, mono- or polyhalo($C_1$-$C_4$ alkyl) radicals, $C_1$-$C_4$ alkoxy radicals and mono- or polyhalo ($C_1$-$C_4$ alkoxy) radicals), or a $C_1$-$C_4$ ethynyl, $C_1$-$C_4$ acetynyl, mono- or polyhalo($C_2$-$C_4$ ethynyl) or mono- or polyhalo ($C_2$-$C_4$ acetynyl) radical, $R_{12}$ has one of the meanings of $R_5$, with the exception of C(=O)—$R_{13}$, and $R_4$ denotes a hydrogen atom, a halogen atom, in particular a chlorine or bromine atom, a $C_1$-$C_4$ alkyl radical, optionally substituted (e.g. with one or more atoms or radicals such as halogen atoms and $C_1$-$C_4$ alkoxy, mono- or polyhalo($C_1$-$C_4$ alkoxy), $C_2$-$C_4$ alkenyl, $C_2$-$C_4$ alkynyl, mono- or polyhalo($C_2$-$C_4$ alkenyl) and mono- or polyhalo($C_2$-$C_4$ alkynyl) radicals), or $C_3$-$C_7$ cycloalkyl, $C_6$-$C_{10}$ aryl (in particular phenyl) or $C_7$-$C_{11}$ aralkyl (in particular benzyl) radicals, it being possible for these various radicals to be optionally substituted (e.g. with one or more atoms or radicals such as halogen atoms, $C_1$-$C_4$ alkyl radicals, mono- or polyhalo($C_1$-$C_4$ alkyl) radicals, $C_1$-$C_4$ alkoxy radicals and mono- or polyhalo($C_1$-$C_4$ alkoxy) radicals).

The invention also relates to the salified forms of the compounds according to the invention. The salified forms are agriculturally acceptable forms, among which the following may be mentioned: the hydrochloride, sulphate, oxalate, nitrate or arylsulphonate, as well as the addition complexes of these compounds with metal salts, and in particular iron, chromium, copper, manganese, zinc, cobalt, tin, magnesium and aluminium salts.

By way of example, complexes with zinc may be obtained by reacting the compound of formula I with zinc chloride.

Within the meaning of the present text, it is understood that, where no specifed structure is given, the radicals in question can be branched or linear. The term "optionally halogenated" means "optionally mono- or polyhalogenated".

In the formula IA or IB, the symbol

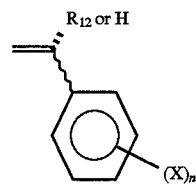

means that the stereochemistry of the double bond can be, without discrimination, E or Z or a mixture of the two. As a result of the steric constraints, the predominant form will be the form in which $R_{12}$ is in the E position with respect to $R_3$ and $R_4$.

The compounds of formula I and the compounds which are usable, where appropriate, by way of intermediates in the reparation processes, and which will be defined when the description of these processes is given, can exist in one or more isomeric forms, depending on the number of asymmetric centres in the molecule. The invention hence relates both to all the optical isomers and to the racemic mixtures thereof and the corresponding diastereoisomers. The separation of the diastereoisomers and/or optical isomers may be performed according to methods known per se.

For the purpose of fungicidal applications, it was found that the invention related preferentially to the compounds of formula IA or IB in which n=1, 2 or 3 and X is preferably a halogen selected from chlorine, bromine or fluorine.

It was also found to be preferable to use the compounds of formula IA or IB in which n=1 or 2, and X is a halogen atom located at the para-position when n=1 and at the meta- and para- or ortho- and para- positions when n=2; preferably, n=1 and X is located at the para-position.

Very advantageously, X is a chlorine atom.

Taking into account the restrictions defined above, applied separately or in combination, it was found to be preferable, in consideration of the fungicidal properties, to use the compounds of formula I in which W is —N=.

Optionally taking into account the restrictions defined above, applied separately or in combination, it was found to be preferable, in consideration of the fungicidal properties, to use the compounds of formula IA or IB in which $R_3$, $R_6$, $R_8$ and $R_{10}$ are a hydrogen atom and $R_4$, $R_7$, $R_9$ and $R_{11}$ are preferably a hydrogen atom or a $C_1$-$C_4$ alkyl radical.

Optionally taking into account the restrictions defined above, applied separately or in combination, it was found to be preferable, in consideration of the fungicidal properties, to use the compounds of formula IA or IB in which $R_1$ and $R_2$ are selected from methyl and ethyl radicals or a hydrogen atom.

Optionally taking into account the restrictions defined above, applied separately or in combination, it was found to be preferable, in consideration of the fungicidal properties, to use the compounds in which $R_5$ is a hydrogen atom or $C_1$-$C_4$ alkyl; very advantageously, $R_5$ is a hydrogen atom.

Optionally taking into account the restrictions defined above, applied separately or in combination, it was found to be preferable, in consideration of the fungicidal properties, to use the compounds in which R12 is a hydrogen atom.

Optionally taking into account the restrictions defined above, applied separately or in combination, it was found to be preferable, in consideration of the fungicidal properties, to use the compounds of formula IA in which A is preferably $CR_6R_7$ or $CR_6R_7CR_8R_9$.

Preferably, on account of their foliar (in particular anti-Botrytis) activity and/or their lack of phytotoxicity, enabling them to be applied as a seed treatment, the triazoles of formula IA in which A is $CR_6R_7$, $R_1$ and $R_2$ are selected from methyl or ethyl radicals, $R_3$, $R_5$ to $R_7$ and $R_{12}$ are a hydrogen atom and $R_4$ is methyl, ethyl, n-propyl, isopropyl or a hydrogen atom, or A is $CR_6R_7$ $CR_8R_9$, $R_1$ and $R_2$ are selected from methyl and ethyl radicals or a hydrogen atom, $R_3$, $R_5$ to $R_9$ and $R_{12}$ are a hydrogen atom and $R_4$ is methyl, ethyl, n-propyl, isopropyl or a hydrogen atom, will be used.

The following compounds are preferred:

2-(4-chlorobenzylidene)-5-methyl-5-ethyl-1-(1H-1,2,4-triazol-1-ylmethyl)-1-cyclopentanol 2-(4-chlorobenzylidene)-5,5-dimethyl-1-(1H-1,2,4-triazol-1-ylmethyl)-1-cyclopentanol 2-(4-chlorobenzylidene)-6-methyl-1-(1H-1,2,4-triazol-1-ylmethyl)-1-cyclohexanol 2-(4-chlorobenzylidene)-6,6-dimethyl-1-(1H-1,2,4-triazol-1-ylmethyl)-1-cyclohexanol 2-(4-chlorobenzylidene)-1-(1H-1,2,4-triazol-1-ylmethyl)-1-cyclohexanol.

The present invention also relates to processes for preparing the compounds according to the invention.

In the description which follows, the substituents described below have the same meaning as those appearing above, except where otherwise stated.

A—The case of the compounds of formula IA

This process consists in reacting the chloride of an omega-alkenoic acid of formula:

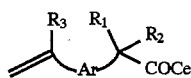

II in which $R_1$ and $R_2$ cannot be a $C_1$–$C_4$ alkyl radical substituted with one or more $C_2$–$C_4$ alkenyl, $C_2$–$C_4$ alkynyl, mono- or polyhalo($C_2$–$C_4$ alkenyl) or mono- or polyhalo ($C_2$–$C_4$ alkynyl) radicals or a $C_1$–$C_4$ alkoxy radicals, in the presence of aluminium chloride, in an inert solvent such as dichloromethane or carbon disulphide or nitromethane, a described in the literature by K. R. KOPECKY et al. in Can. J. Chem. 59, 3273 (1981) and W. C. AGOSTA et al. J. Am. Soc 93, 5513 (1971), so as to obtain a mixture of cycloalkanone and cycloalkenone of formulae:

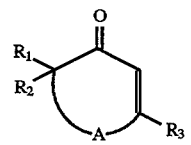

III

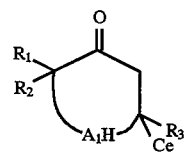

IV

In the compound of formula IV, $A_1H$ corresponds to the groups —$CR_7H$ or —$CR_6R_7$—$CR_9H$ or —$CR_6R_7$—$CR_8R_9$—$CR_{11}H$, and is hence obtained only when A is $A_1H$.

In the case where it is desired to produce the compound of formula V in which $R_4$ is a hydrogen atom, the compound of formula III is then subjected to a catalytic hydrogenation to obtain the compound:

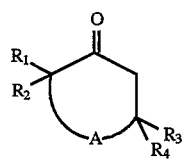

V

In the case where it is desired to produce the compound of formula V above in which $R_4$ is other than a halogen or hydrogen atom, a magnesium derivative of formula $R_4M$ (M=MgHal), obtained in a known manner by reacting, e.g., the compound of formula $R_5I$ with magnesium in the presence of ether, is reacted with a cycloalkenone of formula III in the presence of a catalytic amount of copper iodide at low temperature, in a polar solvent, in a known manner. Water is then added to the mixture in order to isolate the compound of formula V.

The cycloalkanone thereby obtained, of formula (V), in which, it should be recalled, $R_1$ and $R_2$ have the same meaning as in the general formula except that they cannot be a $C_1$–$C_4$ alkyl radical substituted with one or more $C_2$–$C_4$ alkenyl, $C_2$–$C_4$ alkynyl, mono- or polyhalo($C_2$–$C_4$) alkenyl or mono- or polyhalo($C_2$–$C_4$ alkynyl) radicals or a $C_1$–$C_4$ alkoxy radical, $R_4$ has the same meaning as in the general formula except that it cannot be a halogen atom, and $R_3$, $R_6$ and $R_7$ have the same meaning as in the general formula, is subjected to the well-known aldolization/crotonization reaction by condensation with a benzaldehyde of formula:

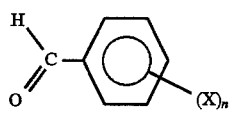

VI so as to obtain compounds of formula VII in which $R_{12}$ is a hydrogen atom:

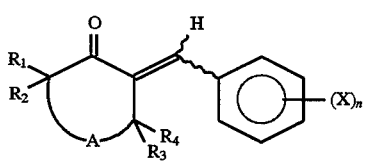

VII

To obtain a compound of formula VII in which $R_{12}$ is other than a hydrogen atom, a silyl ether of formula XI:

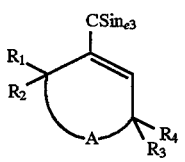

XI is reacted with an acetal of formula XII:

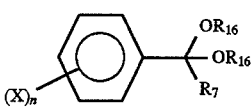

XII in which $R_{16}$ is a $C_1$–$C_4$ alkyl radical, by mixing the acetal of formula XII beforehand with titanium tetrachloride in a halogenated solvent such as dichloromethane at approximately 0° C., followed by addition of the silyl ether of formula XI at approximately 0° C. and subsequent hydrolysis with HCl, as described in T. NUKAIYANA et al. J. Am. Chem. Soc. 1974, 96, 7503.

To obtain a compound of formula VII in which $R_1$ is an alkyl or aralkyl group, optionally substituted, as defined in the general formula, and $R_2$ is other than hydrogen or than a $C_1$–$C_4$ alkyl radical substituted with one or more $C_2$–$C_4$ alkenyl, $C_2$–$C_4$ alkynyl or mono- or polyhalo($C_2$–$C_4$ alkynyl) radicals, another process consists in reacting one of the ketones of formulae III, V and VII, prepared as above, in which $R_1$ is a hydrogen atom and $R_2$ is other than a hydrogen atom or than a $C_1$–$C_4$ alkyl radical substituted with one or more $C_2$–$C_4$ alkenyl, $C_2$–$C_4$ alkynyl or mono- or polyhalo($C_2$–$C_4$ alkynyl) radicals, is reacted with an alkylating agent $R_1$—Y, in which $R_1$ is an alkyl or aralkyl group, optionally substituted, as defined in the general formula, and Y a leaving group such as, e.g., halogen, sulphonate or sulphate, in the presence of an organic or inorganic base, preferably alkali metal or alkaline earth metal hydroxides, alcoholates and hydrides, in a protic or aprotic solvent or mixture of solvents such as saturated, unsaturated or aromatic hydrocarbons, optionally halogenated, alcohols, aides, nitriles or oxygenated solvents derived from sulphides, such as DMSO or sulpholane. Other ketones of formulae III, V and VII are thereby obtained. In the case where ketones of formula III or V have been obtained, which is possible in the case of one of the methods presented above, the conversion procedure described above is then followed in order to arrive at the ketones of formula VII.

To obtain a compound of formula VII in which $R_1$ and $R_2$, identical, are an alkyl or aralkyl group as defined in the general formula, another process consists in reacting a ketone of formula III, V or VII, prepared as above, in which $R_1$ and $R_2$ are a hydrogen atom, with an alkylating agent $R_1$—Y, in which $R_1$ is an alkyl or aralkyl group as defined in the general formula and Y a leaving group such as, e.g., halogen, sulphonate or sulphate, in the presence of an organic or inorganic base, preferably alkali metal or alkaline earth metal hydroxides, alcoholates and hydrides, in a protic or aprotic solvent or mixture of solvents such as saturated, unsaturated or aromatic hydrocarbons, optionally halogenated, alcohols, amides, nitriles or oxygenated solvents derived from sulphides, such as DMSO or sulpholane. It is sometimes possible to isolate the intermediate in which only one of $R_1$ and $R_2$ is an alkyl or aralkyl group as defined above. These compounds VII are then also usable for obtaining the compounds I according to the processes described. In the case where ketones of formula III or V have been obtained, which is possible in the case of one of the methods presented above, the conversion procedure described above is then followed in order to arrive at the ketones of formula VII.

In the case where $R_1$ and $R_2$ form a $C_2$–$C_5$ hydrocarbon chain, a compound of formula Y—$R_9$—Y, $R_9$ being a $C_2$–$C_5$ hydrocarbon radical, optionally substituted (e.g. with one or more atoms or radicals such as halogen atoms, $C_1$–$C_4$ alkyl radicals, mono- or polyhalo($C_1$–$C_4$ alkyl) radicals, $C_1$–$C_4$ alkoxy radicals and mono- or polyhalo($C_1$–$C_4$ alkoxy) radicals), is reacted in the same manner as above with a ketone of formula III, V or VII in which $R_1$ and $R_2$ are a hydrogen atom, according to the process described above.

In the case where $R_1$ and/or $R_2$ is/are an allyl group, another process consists in reacting a ketone of formula V in which $R_1$ and $R_2$ are a hydrogen atom with 2 moles of allyl alcohol and 1 mole of 2,2-dimethoxy-propane, in the presence of a catalytic amount of para-toluenesulphonic acid and in an inert solvent such as toluene, so as to obtain the corresponding monoallyl ketone, as is well described by W. L. Howard and N. B. Lorette, Org. Synth. 42, 34 (1964). This ketone is then reacted with the compound of formula VI as described above, and the addition of another allyl radical is carried out by the method described above by alkylation.

In the case where $R_1$ and/or $R_2$ is/are a $C_1$–$C_4$ alkoxy radical, it is advantageous to start with a cycloalkanone of formula V in which the alkoxy radical or radicals is/are already introduced beforehand by a method known to those versed in the art (e.g. the reaction of α-bromo ketones with alkali metal alcoholates).

Another general process for obtaining the ketones VII for which at least one of $R_1$ and $R_2$ is hydrogen consists in preparing an enamine from a cycloalkanone V in which at least one of $R_1$ and $R_2$ is hydrogen, according to B. C. McKUSICK and F. E. NURFORD Org. Synth. Coll. Vol. V, 808, and condensing this enamine with a benzaldehyde VI according to L. BIRKOFFER, S. M. KIM, H. D. ENGELS Chem. Ber. (1962) 95, 1495. Acid hydrolysis according to this paper then leads to the ketones VII in which at least one of the groups $R_1$ and $R_2$ is hydrogen.

The said compound of formula (VII) is reacted with a sulphonium ylide as described in E. J. COREY and M. CHAYKOVSKY, J. Am. Chem. Soc 87, 1313, (1965) so as to lead to the oxiranes of formula:

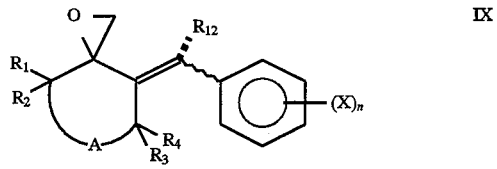

The oxirane of formula (IX) is then reacted with an unsubstituted imidazole or triazole in the presence of an organic or inorganic base, e.g. pyridine, triethylamine, sodium hydroxide, potassium hydroxide, alkali metal or alkaline earth metal carbonates and bicarbonates and alkali metal hydrides, and in a suitable solvent such as, e.g. alcohols, ketones, amides, nitriles and optionally halogenated aromatic hydrocarbons, at a temperature between 80° and the refluxing temperature of the solvent and in a mole ratio IX/imidazole or triazole preferably of between 1.1 and 0.2, leading to the compounds of formula I in which $R_5$ is a hydrogen atom and $R_4$ is other than a halogen atom, the other substituents having the same meaning as that stated in the general formula.

The compounds of formula I in which $R_4$ denotes a halogen atom and $R_5$ is a hydrogen atom are obtained by allyl halogenation of the compounds of formula I in which $R_4$ and $R_5$ are a hydrogen atom, with NBS (N-bromosuccinimide), NCS (N-chlorosuccinimide) or t-BuOCl in CCl4 in the presence of peroxides or UV light, according to L. HORNER and E. H. WINKELMANN, Angew. Chem. 71, 349. (1959).

The compound of formula I in which $R_5$ is other than a hydrogen atom and $R_4$ is other than a halogen atom is obtained by etherification or esterification of the compounds of formula I in which $R_5$ is a hydrogen atom and $R_4$ is other than a halogen atom, according to conventional methods well known to those versed in the art: the ethers may be obtained by treating an alkali metal salt of the alcohol of formula (I) (e.g. a lithium or sodium salt) with the appropriate halide of formula $R_5$Hal. The esters may be obtained in a conventional manner by treating an alkali metal salt of formula (I) with the appropriate acid chloride of formula $R_6C$=OCl or the corresponding anhydride of formula $(R_6)_2O_2C$=O.

The compounds of formula (I) in which $R_4$ is a halogen atom and $R_5$ is other than a hydrogen atom are obtained by, in a first step, esterification or etherification as described above of a compound of formula (I) in which $R_5$ and $R_4$ are a hydrogen atom, followed by halogenation of the resulting compound of formula (I) as described above with, e.g., NBS.

The compounds of formulae XI and XII are obtained in a manner known to those versed in the art. For example, the corresponding benzophenone may be acetalized in an acid medium with an alcohol $R_{10}OH$ in the case of the compound of formula XII. Trimethylsilyl chloride may be added to the corresponding cyclopentanone in the presence of dimethylformamide and triethylamine in the case of the compound of formula XII.

B—The case of the compounds of formula IB

The cyclic ketone of formula (IV) is subjected to the well-known aldolization/crotonization reaction by condensation with a benzaldehyde of formula VI in order to obtain the compound of formula:

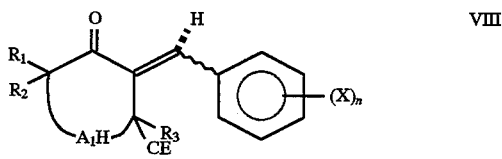

The said compound of formula (VII) is reacted with a sulphonium ylide as described in E. J. COREY and Michael CHAYKOVKSY, J. Am. Chem. Soc 87, 1313, (1965) so as to lead to the oxirane of formula:

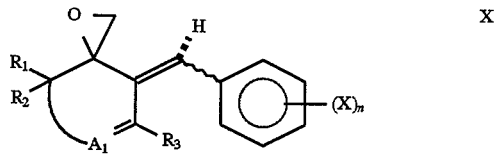

The oxirane of formula (X) is reacted with an unsubstituted imidazole or triazole in the presence of an organic or inorganic base, e.g. pyridine, triethylamine, sodium hydroxide, potassium hydroxide and alkali metal carbonates and bicarbonates, and in a suitable solvent such as, e.g., alcohols, ketones, amides, nitriles and optionally halogenated aromatic hydrocarbons, at a temperature between 80° C. and the refluxing temperature of the solvent and in a mole ratio IX/imidazole or triazole preferably of between 1.1 and 0.2, leading to the compounds of formula IB:

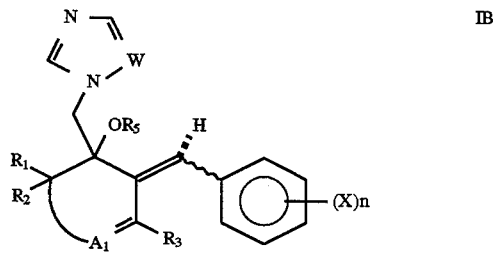

in which $R_5$=H.

The same methods for alkylating or allylating the α-position to the hydroxy ($R_1$, $R_2$) as those described above are applied, and likewise those for obtaining a compound in which $R_5$ is other than H.

Naturally, other preparation processes may also be suitable.

The subject of the invention is also the compounds which are usable, where appropriate, by way of intermediates in the preparation processes described above, and of formulae III, IV, V, VII, VIII, IX and X described above, in which the substituents A, $A_1$, X, n, $R_1$ to $R_5$ and $R_{12}$ have the same meaning as in claim 1.

The present invention also relates to the use of the compounds of formula I by way of fungicides.

The compounds according to the invention may be used for both the preventive and the curative control of fungi, in particular of the basidiomycetes, ascomycetes, adelomycetes or fungi imperfecti type, especially rusts, powdery mildew, eyespot, fusarioses, *Fusarium roseum, Fusarium nivale*, helminthosporioses, rhynchosporioses, septorioses and rhizoctonia diseases of vegetables and plants in general, and especially of cereals such as wheat, barley, rye, oats and hybrids thereof, and also rice and maize. The compounds according to the invention are especially active against fungi, in particular of the basidiomycetes, ascomycetes, adelomycetes or fungi imperfecti type, such as *Botrytis cinerea, Erysiphe graminis, Puccinia recondita, Piricularia oryzae, Cercospora beticola, Puccinia striiformis, Erysiphe cichoracearum, Fusarium oxysporum (melonis), Pyrenophora avenae, Septoria tritici, Venturia inaequalis, Whetzelinia sclerotiorum, Monilia laxa, Mycosphaerella fijiensis, Marssonina panettoniana, Alternaria solani, Aspergillus niger, Cercospora arachidicola, Cladosporium herbarum, Helminthosporium oryzae, Penicillium expansum*, Pestalozzia sp, *Phialophora cinerescens, Phoma betae, Phoma foveata, Phoma lingam, Ustilago maydis, Verticillium dahliae, Ascochyta pisi, Guignardia bidwellii, Corticium rolfsii, Phomopsis viticola, Sclerotinia sclerotiorum, Sclerotinia minor, Coryneum cardinale* and *Rhizoctonia solani*.

They are also active as well against the following fungi: *Acrostalagmus koningi*, Alternaria sp., Colletotrichum sp., *Corticium rolfsii, Diplodia natalensis, Gaeumannomyces graminis, Gibberella fujikuroi, Hormodendron cladosporioides, Lentinus degener* or *tigrinus, Lenzites quercina, Memnoniella echinata, Myrothecium verrucaria, Paecylomyces varioti, Pellicularia sasakii, Phellinus megaloporus, Polystictus sanguineus, Poria vaporaria, Sclerotium rolfsii, Stachybotris atra*, Stereum sp., Stilbum sp., *Trametes trabea, Trichoderma pseudokoningi* and *Trichothecium roseum*.

The compounds of the invention are especially advantageous on account of their broad spectrum in respect of diseases of cereals (powdery mildew, rust, eyespot, helminthosporioses, septorioses and fusarioses). They are also of great importance by reason of their activity against grey mould (Botrytis) and cercosporioses and, as a result, they may be applied on crops as varied as vine, market-garden crops and cultivated trees, and tropical crops such as groundnut, banana, coffee, pecan nut and the like.

In view of their lack of phytotoxicity, the compounds may be used for the protection of the products of multiplication of plants against diseases caused by fungi.

The applicants believe that the benzylidene cycloalkyl structure is important as it permits the bond

C-phenyl to be locked in view of the conjugation. The applicants have noted that omission of the double bond, which corresponds to the 2-phenylethyl structure, leads to phytotoxic fungicidal compositions.

The invention hence relates, in addition, to a product of multiplication of cultivated plants which has undergone a protective treatment with a compound of the invention.

The term "product of multiplication" denotes all the generative parts of the plant which can be used for the multiplication of the latter. There may be mentioned, e.g., the grains (seeds in the narrow sense), roots, fruit, tubers, bulbs, rhizomes, stem parts, seedlings (shoots) and other parts of plants. There may also be mentioned germinated plants and young seedlings which have to be transplanted after germination or after emergence from the soil. These young seedlings can be protected before transplantion by a total or partial treatment by immersion.

In general, these compounds will be applied at the rate of 0.1 g to 500 g per quintal of grain.

Thus, these compounds may be used in the treatment of seeds (e.g. cereals, cotton, beet, rape, grain fooder and vegetable seeds), e.g. in the form of coating or film formation. A form of application may be found in U.S. Pat. No. 3,989,501, col 7, 1 17–23. Likewise in FR-A-2,588,442. Flowables may also be used.

In general, these formulations are already known; see, e.g., "Catalogue of pesticide formulation types and international coding system", published by GIFAP, technical monograph no. 2, pages 12 to 14, revised January 1984.

Apart from the applications already described above, the products according to the invention exhibit, in addition, excellent biocidal activity with respect to many other varieties of microorganisms, among which there may be mentioned, without implied limitation, fungi such as those of the genera:

Pullularia, such as the species *P. pullulans*,
Chaetomium, such as the species *C. globosum*,
Aspergillus, such as the species *Aspergillus niger*, and
Coniophora, such as the species *C. puteana*.

By reason of their biocidal activity, the products of the invention permit effective control of microorganisms whose proliferation creates many problems in agricultural and industrial fields. To this end, they are most especially well suited to the protection of plants or industrial products such as wood, leather, paint, paper, rope, plastics and industrial water circuits.

They are most especially suitable for the protection of lignocellulose products, and in particular of wood, both wood used in furniture and constructional timber and wood exposed to adverse weather conditions, such as fence posts, vine stakes and railway sleepers.

The compounds according to the invention, used alone or in the form of compositions as defined above in the treatment of wood, are generally employed with organic solvents, and can be optionally combined with one or more known biocidal products such as pentachlorophenol, metal salts, in particular of copper, manganese, cobalt, chromium or zinc derived from inorganic or carboxylic acids (heptanoic, octanoic and naphthenic acids); and organotin complexes, mercaptobenzothiazole, and insecticides such as pyrethroids or organochlorine compounds.

The invention also relates to a process for treating crops attacked or liable to be attacked by fungal diseases, wherein an effective dose of a compound of the invention is applied on the leaves.

The compounds are advantageously applied at doses of 0.002 to 5 kg/ha, and more specifically 0.005 to 1 kg/ha.

For their use in practice, the compounds according to the invention are rarely used alone. More often than not, they form part of compositions. These compositions which are usable for the protection of plants against fungal diseases, or in compositions for regulating plant growth, contain as active substance a compound according to the invention, as described above, in combination with agriculturally acceptable solid or liquid vehicles and/or surfactant agents which are also agriculturally acceptable. The usual inert vehicles and the usual surfactant agents are usable, in particular.

These compositions customarily contain between 0.5 and 95% of compound according to the invention.

The term "vehicle" in the present description denotes a natural or synthetic organic or inorganic substance with which the active substance is combined in order to facilitate its application on the plant, on seeds or on the soil. This vehicle is hence generally inert and it must be agriculturally acceptable, in particular on the plant treated. The vehicle can be solid (clays, natural or synthetic silicates, silica, resins, waxes, solid fertilizers, and the like) or liquid (water, alcohols, ketones, petroleum cuts, aromatic or paraffinic hydrocarbons, chlorinated hydrocarbons, liquefied gases, and the like).

The surfactant agent can be an emulsifying, dispersant or wetting agent of the ionic or nonionic type. There may be mentioned, e.g., polyacrylic acid salts, lignosulphonic acid salts, phenolsulphonic or naphthalenesulphonic acid salts, polycondensates of ethylene oxide with fatty alcohols or with fatty acids or with fatty amines, substituted phenols (in particular alkylphenols or arylphenols), salts of sulphosuccinic acid esters, taurine derivatives (in particular alkyl taurides) and polycondensates of ethylene oxide with phosphoric acid esters of alcohols or phenols. The presence of at least one surfactant agent is generally essential when the active substance and/or the inert vehicle are not water-soluble and the carrier agent for the application is water.

These compounds can also contain any other sort of ingredient such as, e.g., protective colloids, adhesives, thickeners, thixotropic agents, penetrating agents, stabilizers, sequestering agents, and the like, as well as other known active substances having pesticidal (and in particular insecticidal or fungicidal) properties or having plant growth-promoting properties (in particular fertilizers) or having plant growth-regulating properties. More generally, the compounds according to the invention may be combined with all solid or liquid additives corresponding to the customary techniques for preparing formulations.

For their application, the compounds of formula (I) are generally in the form of compositions; these compositions according to the invention are themselves in quite diverse solid or liquid forms.

As solid forms of compositions, there may be mentioned powders for dusting or dispersion (having a content of the compound of formula (I) which can range up to 100%) and granules, in particular those obtained by extrusion, by compaction, by impregnation of a granulated vehicle or by granulation from a powder (the content of the compound of formula (I) in these granules being between 1 and 80% for these latter cases).

According to an example of a granule composition, the following constituents are used:

EXAMPLE F 9

| | |
|---|---|
| active substance | 50 g |
| epichlorohydrin | 2.5 g |
| cetyl polyglycol ether | 2.5 g |
| polyethylene glycol | 35 g |
| kaolin (particle size: 0.3 to 0.8 mm) | 910 g |

In this particular case, the active substance is mixed with the epichlorohydrin and the mixture is dissolved with acetone (60 g); the polyethylene glycol and cetyl polyglycol ether are then added. The kaolin is wetted with the solution obtained and the acetone is then evaporated off under vacuum. A microgranule of this kind is advantageously used for controlling soil fungi.

The compounds of formula (I) can also be used in the form of dusting powders; the composition comprising active substance (50 g) and talc (950 g) can also be used; a composition comprising active substance (20 g), finely divided silica (10 g) and talc (970 g) can also be used; these constituents are mixed and ground and the mixture is applied by dusting.

As liquid forms of compositions, or forms intended for making up liquid compositions when they are applied, there may be mentioned solutions, especially water-soluble concentrates, emulsifiable concentrates, emulsions, flowables, aerosols, wettable powders (or powder for spraying) and pastes.

The emulsifiable or soluble concentrates most often comprise 10 to 80% of active substance, the ready-for-application emulsions or solutions, for their part, containing 0.01 to 20% of active substance.

For example, in addition to the solvent, the emulsifiable concentrates can contain, if necessary, 2 to 20% of suitable additives such as the stabilizers, surfactant agents, penetrating agents, corrosion inhibitors, colourings or adhesives mentioned above.

By way of example, there follows the composition of a few concentrates:

EXAMPLE F (FORMULATION) 1

| | |
|---|---|
| active substance | 400 g/l |
| alkali metal dodecylbenzenesulphonate | 24 g/l |
| condensate of nonylphenol with 10 molecules of ethylene oxide | 16 g/l |
| cyclohexanone | 200 g/l |
| aromatic solvent q.s. | 1 liter |

According to another formula for an emulsifiable concentrate, the following are used:

EXAMPLE F 2

| | |
|---|---|
| active substance | 250 g |
| epoxidized vegetable oil | 25 g |
| mixture of alkylarylsulphonate and ether of polyglycol and fatty alcohols | 100 g |
| dimethylformamide | 50 g |
| xylene | 575 g |

From these concentrates, emulsions of any desired concentration, which are especially suitable for application on leaves, may be obtained by dilution with water.

The flowables, also applicable by spraying, are prepared in such a way as to obtain a stable fluid product which does not settle out, and they usually contain from 10 to 75% of active substance, from 0.5 to 15% of surfactant agents, from 0.1 to 10% of thixotropic agents, from 0 to 10% of suitable additives, such as antifoams, corrosion inhibitors, stabilizers, penetrating agents and adhesives and, as a vehicle, water or an organic liquid in which the active substance is sparingly soluble or insoluble: some organic solid substances or inorganic salts can be dissolved in the vehicle in order to assist in preventing sedimentation or as antifreeze for the water.

The wettable powders (or powder for spraying) are usually prepared in such a way that they contain 20 to 95% of active substance, and they usually contain, in addition to the solid vehicle, from 0 to 5% of a wetting agent, from 3 to 10% of a dispersant agent and, if necessary, from 0 to 10% of one or more stabilizers and/or other additives, such as penetrating agents, adhesives or anti-caking agents, colourings and the like.

By way of example, there follow various compositions of wettable powders:

EXAMPLE F 3

| | |
|---|---|
| active substance | 50% |
| calcium lignosulphonate (deflocculant) | 5% |
| isopropylnaphthalenesulphonate (anionic wetting agent) | 1% |
| anti-caking silica | 5% |
| kaolin (filler) | 39% |

Another composition of a 70% strength powder for spraying employs the following constituents:

EXAMPLE F 4

| | |
|---|---|
| active substance | 700 g |
| sodium dibutylnaphthalenesulphonate | 50 g |
| condensation product in the ratio 3:2:1 of naphthalenesulphonic acid, phenolsulphonic acid and formaldehyde | 30 g |
| kaolin | 100 g |
| whiting | 120 g |

Another composition of a 40% strength powder for spraying employs the following constituents:

EXAMPLE F 5

| | |
|---|---|
| active substance | 400 g |
| sodium lignosulphonate | 50 g |
| sodium dibutylnaphthalenesulphonate | 10 g |
| silica | 540 g |

Another composition of a 25% strength powder for spraying employs the following constituents:

EXAMPLE F 6

| | |
|---|---|
| active substance | 250 g |
| calcium lignosulphonate | 45 g |
| mixture of equal parts by weight of whiting and hydroxyethylcellulose | 19 g |
| sodium dibutylnaphthalenesulphonate | 15 g |
| silica | 195 g |
| whiting | 195 g |
| kaolin | 281 g |

Another composition of a 25% strength powder for spraying employs the following constituents:

EXAMPLE F 7

| | |
|---|---|
| active substance | 250 9 |
| isooctylphenoxy-polyoxyethylene-ethanol | 25 g |
| mixture of equal parts by weight of whiting and hydroxyethylcellulose | 17 g |
| sodium aluminosilicate | 543 g |
| kieselguhr | 165 g |

Another composition of a 10% strength powder for spraying employs the following constituents:

EXAMPLE F 8

| | |
|---|---|
| active substance | 100 g |
| mixture of sodium salts of sulphates of saturated fatty acids | 30 g |
| condensation product of naphthalene-sulphonic acid and formaldehyde | 50 g |
| kaolin | 820 g |

To obtain these powders for spraying or wettable powders, the active substances are mixed intimately in suitable blenders with the additional substances and the mixtures are ground with mills or other suitable grinders. Powders for spraying are thereby obtained, whose wettability and suspendibility are advantageous; they may be suspended in water at any desired concentration and these suspensions are very advantageously usable, especially for application on the leaves of plants.

In place of wettable powders, pastes can be made. The conditions and procedures for making and using these pastes are similar to those for the wettable powders or powders for spraying.

As already stated, the aqueous emulsions and dispersions, e.g. the compositions obtained by diluting with water a wettable powder or an emulsifiable concentrate according to the invention, are included within the general scope of the present invention. The emulsions can be of water-in-oil or oil-in-water type, and they can have a thick consistency like that of "mayonnaise".

In the case of the use of the compounds according to the invention as fungicides, the doses at which these compounds are used can vary within wide limits, in particular according to the virulence of the fungi and the climatic conditions.

Generally speaking, compositions containing 0.5 to 5,000 ppm of active substance are very suitable; these values are indicated for the ready-for-application compositions. Ppm means "parts per million". The range from 0.5 to 5,000 ppm corresponds to a range of $5 \times 10^{-5}$ to 0.5% (percentages by weight).

As regards the compositions suited to storage and transport, they contain, more advantageoulsy, from 0.5 to 95% (by weight) of active substance.

Thus, the compositions for agricultural use according to the invention can contain the active substances according to the invention within very wide limits, ranging from $5 \times 10^{-5}$% to 95% (by weight).

The examples which follow illustrate particular methods of preparation of the compounds according to the invention, as well as these compounds themselves.

EXAMPLE I

Preparation of 2-(4-chlorobenzylidene)-5,5-dimethyl-1-(1H-1,2,4-triazol-1-ylmethyl)-1-cyclopentanol 10% strength aqueous sodium hydroxide solution (100 cc) is added to a mixture of 2,2-dimethylcyclo-pentanone (10 g) and 4-chlorobenzaldehyde (13.8 g) in ethanol (100 cc) at 0° C. After 30 minutes, a thick slurry is filtered and the solid washed and then dried. 2,2-Dimethyl-5-(4-chlorobenzylidene)-1-cyclopentanone (12.5 g), m.p. 120° C., is obtained. This compound, dissolved in THF (50 cc) is added to a solution formed in the following manner: sodium hydride (1.9 g; 80% strength dispersion in mineral oil) in anhydrous DMSO (50 cc) is heated to 80° until the solid has dissolved completely. The solution is then diluted with TEF (100 cc) and thereafter cooled to −10° C. A solution of trimethylsulphonium iodide (11.5 g) in dimethyl sulphoxide (80 cc) is added to the mixture in the course of 10 minutes and the mixture is stirred for 15 minutes at −10° C. A solution of 2,2-dimethyl-4-chloro-5-(4-chlorobenzylidene)-1-cyclopentanone (11.8) is then added in TEF (100 cc).

The mixture thereby produced is left at room temperature, then poured into water and extracted with ether, washed with water, dried and distilled. 7-(4-Chlorobenzylidene)-4,4-dimethyl-1-oxaspiro[2.4]heptane, used directly for the next step, is obtained.

A mixture of the product (5 g) with 1,2,4-triazole (2.8 g) and potassium carbonate (11 g) is heated in N,N-dimethylformamide (40 cc) for 4 hours. The mixture is poured into water and extracted with ethylacetate. The organic phase is washed, dried and recrystallized to obtain the product indicated, m.p. 154° C. (compound no. 1).

In the same manner, the following compounds were obtained:

2-(4-fluorobenzylidene)-5,5-dimethyl-1-(1H-1,2,4-triazol-1-ylmethyl)-1-cyclopentanol (m.p. 147° C.), compound no. 2

2-(2,4-dichlorobenzylidene)-5,5-dimethyl-1-(1H-1,2,4-triazol-1-ylmethyl)-1-cyclopentanol (m.p. 130° C.), compound no. 3

2-(4-trifluoromethylbenzylidene)-5,5-dimethyl-1-(1H-1,2,4-triazol-1-ylmethyl)-1-cyclopentanol (m.p. 132° C.), compound no. 4

2-(4-chlorobenzylidene)-1-(1H-1,2,4-triazol-1-ylmethyl)-1-cyclopentanol (oil), compound no. 5

2-benzylidene-1-(1H-1,2,4-triazol-1-ylmethyl)-1-cyclopentanol (oil), compound no. 6

2-(4-bromobenzylidene)-5,5-dimethyl-1-(1H-1,2,4-triazol-1-ylmethyl)-1-cyclopentanol (m.p. 152° C.), compound no. 7

2-benzylidene-5,5-dimethyl-1-(1H-1,2,4-triazol-1-ylmethyl)-1-cyclopentanol (m.p. 137° C.), compound no. 8

2-(3,4-dichlorobenzylidene)-5,5-dimethyl-1-(1H-1,2,4-triazol-1-ylmethyl)-1-cyclopentanol (m.p. 157° C.), compound no. 9

2-(4-chlorobenzylidene)-5-methyl-1-(1H-1,2,4-triazol-1-ylmethyl)-1-cyclopentanol (oil), compound no. 10

2-(2-chlorobenzylidene)-5,5-dimethyl-1-(1H-1,2,4-triazol-1-ylmethyl)-1-cyclopentanol (oil), compound no. 11

2-(4-phenylbenzylidene)-5,5-dimethyl-1-(1H-1,2,4-triazol-1-ylmethyl)-1-cyclopentanol (m.p. 167° C.), compound no. 12

2-(4-chlorobenzylidene)-5-methyl-5-ethyl-1-(1H-1,2,4-triazol-1-ylmethyl)-1-cyclopentanol (m.p. 144° C.), compound no. 13

2-(4-chlorobenzylidene)-5,5-dimethyl-1-(1H-1,2,4-triazol-1-ylmethyl)-1-methoxy-cyclopentane (m.p. 84° C.), compound no. 14

2-(4-chlorobenzylidene)-4,5,5-trimethyl-1-(1H-1,2,4,-triazol-1-ylmethyl)-1-cyclopentanol (m.p. 148° C.), compound no. 15

2-(4-chlorobenzylidene)-5-methyl-5-methoxymethyl-1-(1H-1,2,4-triazol-1-ylmethyl)-1-cyclopentanol (m.p. 109° C.), compound no. 16

2-(4-chlorobenzylidene)-5,5-di-n-propyl-1-(1H-1,2,4-triazol-1-ylmethyl)-1-cyclopentanol (m.p. 123° C.), compound no. 17

2-(4-chlorobenzylidene)-5,5-diethyl-1-(1H-1,2,4-triazol-1-ylmethyl)-1-cyclopentanol (m.p. 171° C.), compound no. 18

2-(4-fluorobenzylidene)-5,5-diethyl-1-(1H-1,2,4-triazol-1-ylmethyl)-1-cyclopentanol (m.p. 166° C.), compound no. 19

2-(4-fluorobenzylidene)-5,5-di-n-propyl-1-(1H-1,2,4-triazol-1-ylmethyl)-1-cyclopentanol (m.p. 127° C.), compound no. 20

2-(4-cyanobenzylidene)-5,5-dimethyl-1-(1H-1,2,4-triazol-1-ylmethyl)-1-cyclopentanol (m.p. 137° C.), compound no. 21

2-(4-chlorobenzylidene)-5,5-dimethyl-3-ethyl-1-(1H-1,2,4-triazol-1-ylmethyl)-1-cyclopentanol (m.p. 58° C.), compound no. 22

2-(4-parachlorophenoxybenzylidene)-5,5-dimethyl-1-(1H-1,2,4-triazol-1-ylmethyl)-1-cyclopentanol (m.p. 112° C.), compound no. 23

2-(4-chlorobenzylidene)-3-isopropyl-5,5-dimethyl-1-(1H-1,2,4-triazol-1-ylmethyl)-1-cyclopentanol (oil), compound no. 24

EXAMPLE II

Preparation of 2-(4-chlorobenzylidene)-5,5-dimethyl-1-(1H-imidazolylmethyl)-1-cyclopentanol A mixture of 7-(4-chlorobenzylidene)-4,4-dimethyl-1-oxaspiro[2.4]heptane (5 g), produced according to the previous example, with imidazole (2.8 g) and potassium carbonate (11 g) is heated in N,N-dimethylformamide (40 cc) for 4 hours. The mixture is poured into water and extracted with ethyl acetate. The organic phase is washed, dried and recrystallized to obtain the product indicated, m.p. 174° C., compound no. 25.

In the same manner, the following compounds were obtained:

2-(4-fluorobenzylidene)-5,5-dimethyl-1-(1H-imidazolylmethyl)-1-cyclopentanol (m.p. 160° C.), compound no. 26

2-(2,4-dichlorobenzylidene)-5,5-dimethyl-1-(1H-imidazolylmethyl)-1-cyclopentanol (m.p. 134° C.), compound no. 127

2-(4-trifluoromethylbenzylidene)-5,5-dimethyl-1-(1H-imidazolylmethyl)-1-cyclopentanol (m.p. 171° C.), compound no. 28

EXAMPLE III

Preparation of 2-(4-fluorobenzylidene)-5,5-dimethyl-1-(1H-1,2,4-triazol-1-ylmethyl)-1-hydroxy-3-cyclopentene 10% strength aqueous sodium hydroxide solution (50 cc) is added to a mixture of 2,2-dimethyl-4-chloro-1-cyclopentanone (10 g) and 4-fluorobenzaldehyde (8.4 g) in ethanol (100 cc) at 0° C. After 30 minutes, a thick slurry is filtered and the solid washed and then dried. 2,2-Dimethyl-4-chloro-5-(4-fluorobenzylidene)-1-cyclopentanone (11.8 g), m.p. 69° C., is obtained. Sodium hydride (3.1 g; 80% strength dispersion in mineral oil) in anhydrous DMSO (50 cc) is heated to 80° C. until the solid is dissolved completely. The solution is then diluted with THF (100 cc) and thereafter cooled to −10° C. A solution of trimethylsulphonium iodide (11.5 g) in dimethyl sulphoxide (80 cc) is added to the mixture in the course of 10 minutes and the mixture is stirred for 15 minutes at −10° C. A solution of 2,2-dimethyl-4-chloro-5-(4-fluorobenzylidene)-1-cyclopentanone (11.8 g) is then added in THF (100 cc). The mixture thereby produced is left at room temperature, then poured into water and extracted with ether, washed with water, dried and distilled.

7-(4-Fluorobenzylidene)-4,4-dimethyl-1-oxaspiro[2.4]hept-5-ene, used directly for the next step, is obtained.

A mixture of the product obtained (5.5 g) with 1,2,4-triazole (2 g) and potassium carbonate (6.6 g) is heated in N,N-dimethylformamide (50 cc) for 4 hours. The mixture is poured into water and extracted with ethyl acetate. The organic phase is washed, dried and recrystallized to obtain the product indicated (2.4 g), m.p. 168° C., compound no. 29.

In the same manner, the following compounds were obtained:

2-(4-chlorobenzylidene)-5,5-dimethyl-1-(1H-1,2,4-triazol-1-ylmethyl)-1-hydroxy-3-cyclopentene (m.p. 203° C.), compound no. 30

2-(2,4-dichlorobenzylidene)-5,5-dimethyl-1-(1H-1,2,4-triazol-1-ylmethyl)-1-hydroxy-3-cyclopentene (m.p. 182° C.), compound no. 31

EXAMPLE IV

Preparation of 2-(4-fluorobenzylidene)-5,5-dimethyl-1-(1H-imidazolylmethyl)-1-hydroxy-3-cyclopentene A mixture of 7-(4-fluorobenzylidene)-4,4-dimethyl-1-oxaspiro[2.4]hept-5-ene (5.5 g), produced according to the previous example, with imidazole (2 g) and potassium carbonate (6.6 g) is heated in N,N-dimethyl-formamide (50 cc) for 4 hours. The mixture is poured into water and extracted with ethyl acetate. The organic phase is washed, dried and recrystallized to obtain the product indicated, m.p. 172° C., compound no. 32

EXAMPLE V

Preparation of 2-(4-chlorobenzylidene)-3,5,5-trimethyl-1-(1H-1,2,4-triazol-1-ylmethyl)-1-cyclopentanol A mixture of sodium hydride (2.3 g) and DMSO (120 cc) is heated to 75° C. until the solid has dissolved. THF (120 cc) is added and the solution is cooled to −5° C. Trimethylsulphonium iodide (16 g) in DMSO (50 cc) is added while the temperature is maintained below 0° C. 2-(4-Chlorobenzylidene)-3,5,5-trimethylcyclopentanone (15.8 g), dissolved in TFF (20 cc), is added and the solution is left at room temperature.

A solution of triazolylsodium is prepared from 1H-1,2,4-triazole (5.3 g) and sodium hydride (2.3 g) in DMSO (100 cc) and added, and the mixture is then heated to 130° C. for 2 hours. The solution is washed with water, extracted with ethyl acetate, dried and purified on silica. A yellow solid (2.4 g), m.p. 148° C., is obtained.

2-(4-Chlorobenzylidene)-3,5,5-trimethylcyclo-pentanone is obtained in the following manner:

Methyl iodide (7 cc) is added to magnesium (2.7 g) in ether (50 cc). When the organomagnesium derivative is formed, the solution is cooled to −5° C. and cuprous iodide (1 g) is added. 5,5-Dimethyl-2-cyclopentenone (10 g) in ether (30 cc) is added while the temperature is maintained below 0° C. Chlorobenzaldehyde (14 g) in ether is then added. Concentrated hydrochloric acid (50 cc) is then added, followed by water (50 cc). The aqueous phase is then extracted with ether. The organic phase is washed, dried and purified on a silica column. An oily product (15.8 g) is obtained. 5,5-Dimethyl-2-cyclopentenone is obtained in a known manner.

EXAMPLE VI

Preparation of 2-(4-chlorobenzylidene)-5,5-diallyl-1-(1H-1,2,4-triazol-1-ylmethyl)-1-cyclopentanol A mixture of sodium hydride (2.7 g) and DMSO (120 cc) is heated to 75° C. until dissolution has taken place. THF (120 cc) is added and the solution is cooled to −5° C. Trimethylsulphonium iodide (12.6 g) in DMSO (50 cc) is added while the temperature is maintained below 0° C. 2-(4-Chlorobenzylidene)-5,5-diallyl cyclo-pentanone (16.5 g) in THF (20 cc) is added and the solution is left at room temperature.

A solution of triazolylsodium, prepared from 1H-1,2,4-triazole (8.3 g) and sodium hydride (4.8 g) in DMSO (100 cc) is added and the mixture is then heated to 80° C. for 2 hours. The solution is washed with water, extracted with ethyl acetate, dried and purified on a silica column. A yellow solid (6.2 g), m.p. 128° C., is obtained. Compound no. 33.

2-(4-Chlorobenzylidene)-5,5-diallylcyclopentanone is obtained in the following manner:

Sodium hydride (2.5 g) is washed with heptane (50 cc). Toluene (100 cc) and tert-amyl alcohol (6.7 cc) are added and the mixture is heated to 50° C. When the evolution of hydrogen has ceased, 2-(4-Chlorobenzylidene)-5-allylcyclopentanone (15 g) and allyl chloride (8.1 cc) are added. The solution is heated to reflux, cooled and washed with water. The organic phase is dried. After evaporation, a liquid product (16.5 g) is obtained. 5-Allylcyclopentanone is obtained according to W. L. Howard and N. B. Lorette Org. Synth. 42, 34.

In the same manner, 2-(4-fluorobenzylidene)-5,5-diallyl-1-(1H-1,2,4-triazol-1-ylmethyl)-1-cyclopentanol, m.p. 112° C., was obtained. Compound no. 34.

EXAMPLE VII

Preparation of 2-(4-chlorobenzylidene)-5,5-dimethyl-1-(1H-1,2,4-triazol-1-ylmethyl)-1-methoxy cyclopentanol Powdered potassium hydroxide (4.2 g) and 2-(4-chlorobenzylidene)-5,5-dimethyl-1-(1H-1,2,4-thiazolylmethyl)-1-cyclopentanol (5.2 g) in DMSO (32 cc) are stirred at room temperature. Methyl iodide (2 cc) is added and the mixture is stirred. The solution is poured into water and extracted with ethyl acetate. The organic phase is again washed with water and dried. After purification on a silica column, a pure product (4.9 g), m.p. 84° C., is obtained.

2-(4-Chlorobenzylidene)-5,5-dimethyl-1-(1H-1,2,4-thiazolylmethyl)-1-cyclopentanol is obtained in the following manner:

10% strength sodium hydroxide solution (100 cc) is added to a mixture of 2,2-dimethylcyclo pentanone (10 g) and 4-chlorobenzaldehyde (13.8 g) in ethanol (100 cc) at 0° C. After 10 minutes, the thick slurry is filtered and the solid washed and then dried. 2,2-Dimethyl-5-(4-chlorobenzylidene)-1-cyclopentanone (12.5 g), m.p. 120° C., is obtained.

This compound, dissolved in THF (50 cc) is added to a solution formed in the following manner: sodium hydride (1.9 g; 80% strength dispersion in mineral oil) in anhydrous DMSO (50 cc) is heated to 80° C. until the solid has dissolved completely. The solution is then diluted with THF (100 cc) and thereafter cooled to −10° C. A solution of trimethylsulphonium iodide (11.5 g) in dimethyl sulphoxide (80 cc) is added to the mixture in the course of 10 minutes and the mixture is stirred for 15 minutes at −10° C. This solution of 2,2-dimethyl-4-chloro-5-(4-chlorobenzylidene)-1-cyclo-pentanone (11.8 g) is then added in THF (100 cc). The mixture thereby produced is left at room temperature, then poured into water and extracted with ether, washed with water, dried and distilled. 7-(4-Chlorobenzylidene)-4,4-dimethyl-1-oxaspiro[2.4]heptane, used directly for the next step, is obtained. A mixture of the product (5 g) with 1,2,4-triazole (2.8 g) and potassium carbonate (11 g) is heated in N,N-dimethylformamide (40 cc) for 4 hours. The mixture is poured into water and extracted with ethyl acetate. The organic phase is washed, dried and recrystallized to obtain the product indicated, m.p. 154° C. Compound no. 1.

For information, the melting points of the following compounds are given:

2,2-dimethyl-4-chloro-5-(4-fluorobenzylidene)-1-cyclopentanone, m.p. 69° C.

2,2-dimethyl-4-chloro-5-(4-chlorobenzylidene)-1-cyclopentanone, m.p. 68° C.

2,2-dimethyl-4-chloro-5-(2,4-dichlorobenzylidene)-1-cyclopentanone, m.p. 68° C.

2,2-dimethyl-5-(4-fluorobenzylidene)-1-cyclopentanone, m.p. 69° C.

2,2-dimethyl-4-chloro-5-(4-chlorobenzylidene)-1-cyclopentanone, m.p. 120° C.

2,2-dimethyl-5-(4-trifluoromethylbenzylidene)-1-cyclopentanone, m.p. 107° C.

2,2-dimethyl-5-(2,4-dichlorobenzylidene)-1-cyclopentanone, which is an oil.

2,2-dimethyl-4-chloro-5-(4-chlorobenzylidene)-1-cyclopentanone, m.p. 60° C.

2-(4-chlorobenzylidene)-1-cyclopentanone, m.p. 63° C.

2-benzylidene-1-cyclopentanone, which is an oil.

2-(4-bromobenzylidene)-1-cyclopentanone, m.p. 97° C.

2,2-dimethyl-5-benzylidene-1-cyclopentanone, which is an oil.

2,2-dimethyl-5-(3,4-dichlorobenzylidene)-1-cyclopentanone, which is an oil.

2-(3,4-dichlorobenzylidene)-1-cyclopentanone, which is an oil.

2-methyl-5-(4-chlorobenzylidene)-1-cyclopentanone, m.p. 107° C.

2-methyl-5-(2-chlorobenzylidene)-1-cyclopentanone, which is an oil.

2,2-dimethyl-5-(2-chlorobenzylidene)-1-cyclopentanone, which is an oil.

2-phenylbenzylidene-1-cyclopentanone, m.p. 146° C.

2,2-dimethyl-5-phenylbenzylidene-1-cyclopentanone, m.p. 120° C.

2-ethyl-2-methyl-5-(4-chlorobenzylidene)-1-cyclopentanone, m.p. 85° C.

2-allyl-5-(4-chlorobenzylidene)-1-cyclopentanone, m.p. 60° C.

2,2-diallyl-5-(4-chlorobenzylidene)-1-cyclopentanone, which is an oil.

2,2,4-trimethyl-5-(4-chlorobenzylidene)-1-cyclopentanone, which is an oil.

2-methyl-2-methoxymethyl-5-(4-chlorobenzylidene)-1-cyclopentanone, which is an oil.

2-allyl-5-(4-fluorobenzylidene)-1-cyclopentanone, m.p. 111° C.

2,2-diallyl-5-(4-fluorobenzylidene)-1-cyclopentanone, which is an oil.

2,2-diethyl-5-(4-chlorobenzylidene)-1-cyclopentanone, which is an oil.

2,2-diethyl-5-(4-fluorobenzylidene)-1-cyclopentanone, which is an oil.

2-(4-cyanobenzylidene)-1-cyclopentanone, which is an oil.

2,2-dimethyl-5-(4-cyanobenzylidene)-1-cyclopentanone, which is an oil.

2,2-dimethyl-4-ethyl-5-(4-chlorobenzylidene)-1-cyclopentanone, which is an oil.

2-(4-p-chlorophenoxybenzylidene)-1-cyclopentanone, m.p. 92° C.

2,2-dimethyl-5-(4-p-chlorophenoxybenzylidene)-1-cyclopentanone, which is an oil.

2,2-dimethyl-4-isopropyl-5-(4-chlorobenzylidene)-1-cyclopentanone, which is an oil.

2,2-dimethyl-5-(4-chlorobenzylidene)-1-cyclopentanone, m.p. 60° C.

2,2-dimethyl-5-(2,4-dichlorobenzylidene)-1-cyclopentanone, m.p. 68° C.

2,2-dimethyl-5-(4-fluorobenzylidene)-1-cyclopentanone, m.p. 69° C.

EXAMPLE VIII

Preparation of 2-(4-chlorobenzylidene)-6-methyl-1-(1H-1,2,4-triazol-1-ylmethyl)-1-cyclohexanols 10% strength aqueous sodium hydroxide solution (100 cc) is added to a mixture of 2-methylcyclohexanone (22.4 g) and para-chlorobenzaldehyde (28.1 g) in ethanol (250 cc) at 0° C. After stirring for 15 h, the medium is diluted with water and extracted with ethyl acetate.

The organic phase, dried over $Na_2SO_4$, is concentrated and the residue chromatographed on silica with a heptane/ethyl acetate (90:10) eluant. A yellow oil is obtained, the latter is crystallized in pentane and gives a pale yellow powder (17.1 g) of 2-(4-chloro-benzylidene)-6-methylcyclohexanone, m.p. 59° C.

This compound (3.8 g), dissolved in anhydrous THF (33 cc), is added to a reaction medium at −5° C. prepared in the following manner:

Sodium hydride (0.8 g; 60% strength dispersion) is heated to 70° C. in dry DMSO (26 cc) and anhydrous THF (33 cc) is then added. The mixture, cooled to −5° C., is treated with trimethylsulphonium iodide (3.9 g) dissolved in dry DMSO (20 cc).

After 1 hour at −5° C., the 8-(4-chlorobenzylidene)-4-methyl-1-oxaspiro[2.5]octane thereby formed is treated with triazole (2.2 g) and triazolylsodium (0.2 g).

The medium is heated to 93° for 1 h 30 min after distillation of THF (30 cc) and addition of DMF (50 cc).

After dilution with water (1 l), the products are extracted with dichloromethane, and the residue obtained on evaporation is purified by chromatography (eluant: heptane/ethyl acetate, 1:1).

The major diastereoisomer which possesses the methyl substituent and the hydroxyl in the cis relative position, m.p. 139° (compound no. 35), is obtained first, followed by the minor diastereoisomer which possesses the methyl substituent and the hydroxyl in the trans relative position, in the form of a syrup (compound no. 36).

The stereochemistry is assigned by nuclear magnetic resonance according to techniques well known to those versed in the art.

EXAMPLE IX

Preparation of 2-(4-chlorobenzylidene)-6,6-dimethyl-1-(1H-1,2,4-triazol-1-ylmethyl)-1-cyclohexanol 2-(4-Chlorobenzylidene)-6-methylcyclohexanone (7.0 g), prepared above, and then methyl iodide (5.1 g) are added successively to a reaction medium prepared from toluene (25 cc), tert-amyl alcohol (3.6 cc) and sodium hydride (1.35 g of 60% strength dispersion in oil) and heated to 45° C. The mixture is brought to reflux (1 h), poured into water and extracted with ethyl acetate. After drying and concentration, the residue is recrystallized in methanol to give 2-(4-chlorobenzylidene)-6,6-dimethylcyclohexanone (4.7 g), m.p. 92°.

The procedure of Example I is then applied to this ketone (4 g) to lead, after chromatography, to the expected product, m.p. 179° C. (compound no. 37).

In the same manner, the following compounds were obtained:

2-(4-fluorobenzylidene)-6,6-dimethyl-1-(1H-1,2,4-triazol-1-ylmethyl)-1-cyclohexanol. Isomer A. Compound no. 38. M.p. 154° C.

2-(4-chlorobenzylidene)-1-(1H-1,2,4-triazol-1-ylmethyl)-1-cyclohexanol. Isomer A. Compound no. 39. M.p. 117° C.

2-(4-chlorobenzylidene)-6-cyclohexyl-1-(1H-1,2,4-triazol-1-ylmethyl)-1-cyclohexanol. Isomer A. Compound no. 40. M.p. 206° C.

2-(4-chlorobenzylidene)-6-cyclohexyl-1-(1H-1,2,4-triazol-1-ylmethyl)-1-cyclohexanol. Isomer B. Compound no. 41. M.p. 197° C.

2-(4-chlorobenzylidene)-6-t-butyl-1-(1H-1,2,4-triazol-1-ylmethyl)-1-cyclohexanol. Isomer A. Compound no. 42. M.p. 144° C.

2-(4-chlorobenzylidene)-6-sec-butyl-1-(1H-1,2,4-triazol-1-ylmethyl)-1-cyclohexanol-Isomers A+B. Compound no. 43. M.p. 171° C.

2-(4-chlorobenzylidene)-6-sec-butyl-1-(1H-1,2,4-triazol-1-ylmethyl)-1-cyclohexanol. Isomers C+D. Compound no. 44. M.p. 148° C.

2-(4-chlorobenzylidene)-6-methyl-6-phenyl-1-(1H-1,2,4-triazol-1-ylmethyl)-1-cyclohexanol. Isomer A. Compound no. 45. M.p. 177° C.

2-(4-chlorobenzylidene)-6-methyl-6-phenyl-1-(1H-1,2,4-triazol-1-ylmethyl)-1-cyclohexanol. Isomer B. Compound no. 46. M.p. 133° C.

2-(4-chlorobenzylidene)-6-methyl-6-ethyl-1-(1H-1,2,4-triazol-1-ylmethyl)-1-cyclohexanol. Isomers A+B. Compound no. 47. M.p. 175° C.

2-(4-chlorobenzylidene)-6-methyl-6-isopropyl-1-(1H-1,2,4-triazol-1-ylmethyl)-1-cyclohexanol. Isomer A. Compound no. 48. M.p. 154° C.

2-(4-chlorobenzylidene)-6-methyl-6-isobutyl-1-(1H-1,2,4-triazol-1-ylmethyl)-1-cyclohexanol. Isomer A. Compound no. 49. M.p. 163° C.

2-(4-chlorobenzylidene)-6-methyl-6-1-(1H-1,2,4-triazol-1-ylmethyl)-1-cyclohexanol. Isomer B. Compound no. 50. M.p. 184° C.

2-(4-chlorobenzylidene)-1-(1H-1,2,4-triazol-1-ylmethyl)-1-cycloheptanol. Compound no. 54. M.p. 104° C.

2-(4-chlorobenzylidene)-7,7-dimethyl-1-(1H-1,2,4-triazol-1-ylmethyl)-1-cycloheptanol. Compound no. 54. M.p. 143° C.

2-(4-fluorobenzylidene)-1-(1H-1,2,4-triazol-1-ylmethyl)-1-cycloheptanol. Compound no. 56. M.p. 91° C.

2-(4-chlorobenzylidene)-7-methyl-1-(1H-1,2,4-triazol-1-ylmethyl)-1-cycloheptanol. Compound no. 56. M.p. 166° C.

For information, the properties of a few starting cycloalkanones are given below. The reader will note that general methods for preparing these compounds are described in the literature. Reference may usefully be made to the following documents:

German Offenlegungsschrift 2,245,518

D. A. WHITING J., Chem. Soc (1971), 3396

G. Le GUILLANTON (1969), Bull. Soc. Chem, 2871

PAL PERJESI et al. Chem. Bet. (1987), 120, 1449.

J. M. CONIA et al. Bull. Soc. Chem. (1970), 72.

2-(4-fluorobenzylidene)-1-cyclohexanone, b.p. 140° C. at 0.02 mm Hg.

2-(4-chlorobenzylidene)-1-cyclohexanone, m.p. 54° C.

2-methyl-6-(4-chlorobenzylidene)-1-cyclohexanone, m.p. 59° C.

2,2-dimethyl-6-(4-chlorobenzylidene)-1-cyclohexanone, m.p. 92° C.

2,2-dimethyl-6-(4-fluorobenzylidene)-1-cyclohexanone, m.p. 51° C.

2-cyclohexyl-6-(4-chlorobenzylidene)-1-cyclohexanone, m.p. 97° C.

2-t-butyl-6-(4-chlorobenzylidene)-1-cyclohexanone, b.p. 180° C. at 0.06 mm Hg.

2-sec-butyl-6-(4-chlorobenzylidene)-1-cyclohexanone, m.p. 46° C.

2-phenyl-6-(4-chlorobenzylidene)-1-cyclohexanone, m.p. 121° C.

2-methyl-2ophenyl-6-(4-chlorobenzylidene)-1-cyclohexanone, m.p. 77° C.

1,1-dimethyl-3-(4-chlorobenzylidene)-2-tetralone, which is an oil.

2-methyl-2-ethyl-6-(4-chlorobenzylidene)-1-cyclohexanone, m.p. 70° C.

2-methyl-2-isobutyl-6-(4-chlorobenzylidene)-1-cyclohexanone, which is an oil.

2-methyl-2-isopropyl-6-(4-chlorobenzylidene)-1-cyclohexanone, which is an oil.

6-(4-chlorobenzylidene)spiro[4.5]decan-5-one, which is an oil.

2-(4-fluorobenzylidene)-1-cycloheptanone, m.p. 62° C.

2-(4-chlorobenzylidene)-1-cycloheptanone, m.p. 75° C.

2-methyl-7-(4-chlorobenzylidene)-1-cycloheptanone, m.p. 74° C.

2,2-diethyl-7-(4-chlorobenzylidene)-1-cycloheptanone, m.p. 63° C.

2,2-dimethyl-7-(4-chlorobenzylidene)-1-cyclohexanone, m.p. 63° C.

The examples which follow illustrate fungicidal applications of the compounds according to the invention.

In these examples, spraying of solutions or suspensions of active substances is performed under conditions such that the spraying of a solution or suspension of concentration equal to 1 g/l corresponds on average to the application of approximately 2 micrograms of active substance per cm² of plant leaf.

Under the conditions of Examples X to XVI, the compounds illustrated exhibited no phytotoxicity.

In these examples, a product is considered to exert complete protection with respect to a fungal disease when protection is at least 95%; protection is considered to be good when it is at least 80% (but less than 95%), to be fairly good when it is at least 70% (but less than 80%) and to be moderate when it is at least 50% (but less than 70%).

In the present description, the percentages are, except where otherwise stated and except for those relating to yields, percentages by weight. In the case where percentages are expressed relative to the stoichiometric amount, they are molar percentages. As regards concentrations, some of the latter are expressed in ppm (parts per million), which corresponds to mg/l.

The experiments were performed at doses of 1 g/l or 0.3 g/l, without this implying prejudgment of the value of the products themselves.

EXAMPLE X

In Vivo Test on *Botrytis Cinerea* on Excised Tomato Leaves

An aqueous emulsion of the active substance under test having the following composition is prepared by fine grinding:

active substance under test: 60 mg

Tween 80 (surfactant agent consisting of an oleate of a polycondensate of a sorbitan derivative with ethylene oxide) diluted to 10% in water: 0.3 cc the mixture is made up to 60 cc with water.

This aqueous emulsion is then diluted with water to obtain the desired concentration.

Tomatoes (Marmande variety) cultivated in a greenhouse, from 30 to 40 days old, are treated by spraying with aqueous emulsions (referred to as slurries) as defined above and at various concentrations of the compound under test. The experiment is repeated twice with each concentration.

After 24 or 48 hours, the leaves are cut off and placed in 2 Petri dishes (diameter 14 cm), the bottom of which has been lined beforehand with a disc of wet filter paper (5 leaflets per dish).

The inoculum is then introduced using a syringe, by depositing drops (3 drops per leaflet) of a spore suspension. This suspension of Botrytis cinerea spores has been obtained from a 15-day culture, subsequently suspended in a nutrient solution (100,000 units/cc).

The effect is checked 3 and 6 days after contamination, by comparison with an untreated control.

Under these conditions, after 6 days, at a dose of 1 g/l, good or complete protection is observed with the compounds 1 and 3, and at a dose of 0.3 g/l, good or complete protection with the compounds 2, 15, 16, 35, 38 and 39.

EXAMPLE XI

In Vivo Test on *Erysiphe graminis* on Barley (powdery mildew of barley)

Barley, sown in pots on a 50:50 peat/pozzolana earth substrate, is treated at the 10-cm height stage by spraying with an aqueous emulsion (referred to as a slurry), as described above, at the concentration stated below. The experiment is repeated twice. After 24 hours, the barley plants are sprinkled with Erysiphe graminis spores, the sprinkling being performed using diseased plants.

The reading is carried out 8 to 14 days after contamination.

Under these conditions, the following results are observed:

At a dose of 1 g/l, good or complete protection with the compounds 1, 2, 3, 14 and 26, and at 0.3 g/l, with the compounds 4, 11, 38, 53 and 55.

At a dose of 1 g/l, fairly good or moderate protection with the compounds 10, 25 and 33 and, at 0.3 g/l, with the compounds 8, 15, 22, 29 and 39.

EXAMPLE XIII

In Vivo Test on "*Puccinia Recondita*" Responsible for Wheat Rust

Wheat, sown in pots on a 50:50 peat/pozzolana earth substrate, is treated at the 10-cm height stage by spraying with aqueous emulsions (referred to as slurries) of the same composition as that described in Example XI and at various concentrations of the compound under test. The experiment is repeated twice with each concentration.

After 24 hours, an aqueous suspension of spores (50,000 sp/cc) is sprayed onto the wheat; this suspension has been obtained from contaminated plants. The wheat is then placed for 48 hours in an incubation cell at approximately 18° C. and at 100% relative humidity.

25

At the end of these 2 days, the relative humidity is brought back to 60%. A check of the state of the plants is carried out between day 11 and day 15 after contamination, by comparison with the untreated control.

At a dose of 1 g/l, good or complete protection with the compounds 1, 2, 3, 10, 14, 25, 26, 27 and 33, and at 0.3 g/l, with the compounds 4, 7, 9, 13, 14, 15, 18, 19, 28, 34, 35, 37, 38, 43, 47 and 53.

At a dose of 2 g/l, fairly good or moderate protection with the compound 5, and at 0.3 g/l, with the compounds 8, 10, 11, 20, 22, 42, 44 and 49.

EXAMPLE XIII

In Vivo Test on "Piricularia Oryzae" Responsible for Piriculariosis of Rice (rice blast)

Rice, sown in pots in a 50:50 mixture of enriched peat and pozzolana, is treated at the 10-cm height stage by spraying with an aqueous emulsion (referred to as a slurry) defined above having the concentration stated below. The experiment is repeated twice. After 48 hours, the plants are treated, by application on the leaves, with a suspension of spores obtained in a pure culture.

The reading is carried out 8 days after contamination. Under these conditions, the following results are observed:

At a dose of 1 g/l, good or complete protection with the compounds 1, 2, 4, 25 and 28, and at 0.3 g/l, with the compounds 7, 9, 11, 12, 13, 14, 22, 29, 30, 33, 34, 38, 39, 43, 44 and 47.

At a dose of 1 g/l, fairly good or moderate protection with the compounds 5, 26 and 27, and at 0.3 g/l, with the compounds 15, 16, 18, 23, 31, 32, 42, 48 and 49.

EXAMPLE XIV

In Vivo Test on "Puccinia Recondita" by Application as a Seed Treatment

Wheat grain, Talent variety, is treated with the slurry of the previous example at a dose of 75 g/q and sown in a substrate composed of a 50:50 peat/pozzolana earth mixture. 15 days after sowing, the plantlets are inoculated with Puccinia recondita according to the protocol described in Example XII. The reading of the results is carried out 30 days and 45 days after sowing.

At the doses stated, with the compounds nos. 1, 2, 3, 4, 13, 28, 29, 30, 31, 32, 35 and 37, the percentage of infection is zero at 30 days after sowing, the plantlets derived from untreated grain being 100% contaminated.

EXAMPLE XV

In Vivo Test on Fusarium Roseum by Application as a Seed Treatment

Wheat grain, Talent variety, naturally contaminated with Fusarium roseum is treated with a slurry defined above in Example X at doses of 10, 25, 50 and 100 g per 100 kg of grain. From 50 g of treated grain, 200 seeds are deposited on a medium containing agar and malt in concentrations of 2% and 1%, respectively. The seeds are stored for 10 days at 20° C. A check of the state of the seeds is carried out by comparison with the untreated control, on which colonies of Fusarium roseum have grown.

At the doses stated, good or complete protection is observed with the compounds 1, 2, 3, 4, 13, 15, 28, 29, 30, 31, 32, 35, 37, 52 and 54.

26

The example below illustrates the lack of phytotoxicity of compounds according to the invention with respect to the growth of the seeds.

EXAMPLE XVI

Wheat grain, Talent variety, is treated with a slurry at doses of 2.5, 10, 25, 50, 100, 200 and 400 g/q.

The seeds are deposited on a filter paper soaked with water. After 15 days' incubation at 25° C., the lengths of the coleoptiles and of the first leaves are measured for the compounds nos. 1, 13, 15, 35 and 37.

The results are presented in the table below:

| Dose g/q | length (cm) coleoptiles and first leaves |
|---|---|
| 0 | 13 |
| 12 | 13 |
| 25 | 13 |
| 50 | 13 |
| 100 | 12 |
| 200 | 13 |
| 400 | 12 |

Each value shown above is the mean of forty plantlets.

We claim:

1. A compound useful as an intermediate in the preparation of a (benzylidene)-azolylmethylcycloalkane or -alkene fungicide of formula:

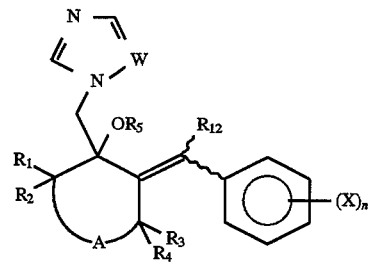

IA

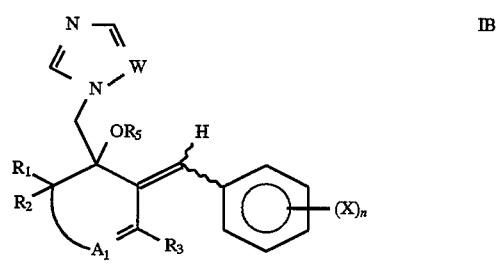

IB in which

A is $-CR_6R_7-$ or $-CR_6R_7CR_8R_9-$ or $-CR_6R_7CR_8R_9CR_{10}R_{13}-$;

$A_1$ is $CR_7=$, $-CR_6R_7-CR_9=$ or $-CR_6R_7-CR_8R_9-CR_{11}=$;

X is a halogen atom, or a cyano or nitro group, or a $C_1$-$C_4$ alkyl or $C_1$-$C_4$ alkoxy group, which is unhalogenated or halogenated;

is zero or a positive integer less than 6, wherein the groups X are identical or different when n is greater than 1;

W denotes a trivalent group consisting of a =CH— group or a nitrogen atom =N—;

$R_1$ and $R_2$, which are identical or different, denote a hydrogen atom; a $C_1$-$C_4$ alkyl radical, which are unsubstituted or substituted with one or more atoms or radicals selected from the group consisting of halogen atoms, $C_1$–$C_4$ alkoxy, mono- or polyhalo($C_1$–$C_4$ alkoxy), $C_2$–$C_4$ alkenyl, $C_2$–$C_4$ alkynyl, mono- or polyhalo($C_2$–$C_4$ alkenyl) and mono- or polyhalo ($C_2$–$C_4$ alkynyl) radicals; a $C_1$–$C_4$ alkoxy radical which is unsubstituted or substituted with one or more atoms or radicals selected from the group consisting of halogen atoms, $C_1$–$C_4$ alkoxy, mono- or polyhalo($C_1$–$C_4$ alkoxy), $C_2$–$C_4$ alkenyl, $C_2$–$C_4$ alkynyl, mono- or polyhalo($C_2$–$C_4$ alkenyl) and mono- or polyhalo ($C_2$–$C_4$ alkynyl) radicals; or $C_3$–$C_7$ cycloalkyl, $C_6$–$C_{10}$ aryl or $C_7$–$C_{11}$ aralkyl radicals, wherein these various radicals are unsubstituted or substituted with one or more atoms or radicals selected from the group consisting of halogen atoms, $C_1$–$C_4$ alkyl radicals, mono- or polyhalo($C_1$–$C_4$ alkyl) radicals, $C_1$–$C_4$ alkoxy radicals and mono- or polyhalo($C_1$–$C_4$ alkoxy) radicals; $R_1$ and $R_2$ together alternatively form a $C_2$–$C_5$ hydrocarbon chain making a ring with the carbon to which $R_1$ and $R_2$ are attached, wherein the chain is unsubstituted or substituted as for the $C_6$–$C_{10}$ aryl radicals, or $R_1$ and $R_2$ together alternatively form a $C_2$–$C_5$ dioxolane hydrocarbon chain with the carbon to which $R_1$ and $R_2$ are attached, wherein the chain is unsubstituted or substituted as for the $C_6$–$C_{10}$ aryl radicals;

$R_3$ and $R_6$ to $R_{11}$, which may be identical or different, denote a hydrogen atom; a $C_1$–$C_4$ alkyl radical which is unsubstituted or substituted with one or more atoms or radicals selected from the group consisting of halogen atoms, $C_1$–$C_4$ alkoxy and mono- or polyhalo ($C_1$–$C_4$ alkoxy) radicals; or $C_3$–$C_7$ cycloalkyl, $C_6$–$C_{10}$ aryl or $C_7$–$C_{11}$ aralkyl radicals, wherein these various radicals are unsubstituted or substituted with one or more atoms or radicals selected from the group consisting of halogen atoms, $C_1$–$C_4$ alkyl radicals, mono- or polyhalo($C_1$–$C_4$ alkyl) radicals, $C_1$–$C_4$ alkoxy radicals and mono- or polyhalo($C_1$–$C_4$ alkoxy) radicals; or alternatively two adjacent radicals of the chain A, together with the atoms of A to which they are attached, form a benzene ring fused to the cycloalkane;

$R_5$ denotes a hydrogen atom; a $C_1$–$C_4$ alkyl radical, which is unsubstituted or substituted with one or more atoms or radicals selected from the group consisting of halogen atoms, $C_1$–$C_4$ alkoxy, mono- or polyhalo($C_1$–$C_4$ alkoxy), $C_2$–$C_4$ alkenyl, $C_2$–$C_4$ alkynyl, mono- or polyhalo($C_2$–$C_4$ alkenyl) and mono- or polyhalo ($C_2$–$C_4$ alkynyl) radicals; or $C_3$–$C_7$ cycloalkyl, $C_6$–$C_{10}$ aryl or $C_7$–$C_{11}$ aralkyl radicals, wherein these various radicals are unsubstituted or substituted with one or more atoms or radicals selected from the group consisting of halogen atoms, $C_1$–$C_4$ alkyl radicals, mono- or polyhalo($C_1$–$C_4$ alkyl) radicals, $C_1$–$C_4$ alkoxy radicals and mono- or polyhalo($C_1$–$C_4$ alkoxy) radicals; or $R_5$ denotes a group $C(=O)$—$R_{13}$, $R_{13}$ denoting a $C_1$–$C_4$ alkyl radical, which is unsubstituted or substituted with one or more atoms or radicals selected from the group consisting of halogen atoms, $C_1$–$C_4$ alkoxy, mono- or polyhalo($C_1$–$C_4$ alkoxy), $C_2$–$C_4$ alkenyl, $C_2$–$C_4$ alkynyl, mono- or polyhalo ($C_2$–$C_4$ alkenyl) and mono- or polyhalo($C_2$–$C_4$ alkynyl) radicals; or $C_3$–$C_7$ cycloalkyl, $C_6$–$C_{10}$ aryl or $C_7$–$C_{11}$ aralkyl radicals, wherein these various radicals are unsubstituted or substituted with one or more atoms or radicals selected from the group consisting of halogen atoms, $C_1$–$C_4$ alkyl radicals, mono- or polyhalo($C_1$–$C_4$ alkyl) radicals, $C_1$–$C_4$ alkoxy radicals and mono- or polyhalo ($C_1$–$C_4$ alkoxy) radicals; or a $C_2$–$C_4$ ethynyl, $C_2$–$C_4$ acetynyl, mono- or polyhalo($C_2$–$C_4$ ethynyl) or mono- or polyhalo($C_2$–$C_4$ acetynyl) radical;

$R_{12}$ has one of the meanings of $R_5$, with the exception of $C(=O)$—$R_{13}$; and $R_4$ denotes a hydrogen atom, a halogen atom, a $C_1$–$C_4$ alkyl radical, which is unsubstituted or substituted with one or more atoms or radicals selected from the group consisting of halogen atoms, $C_1$–$C_4$ alkoxy, mono- or polyhalo($C_1$–$C_4$ alkoxy), $C_2$–$C_4$ alkenyl, $C_2$–$C_4$ alkynyl, mono- or polyhalo($C_2$–$C_4$ alkenyl) and mono- or polyhalo($C_2$–$C_4$ alkynyl) radicals; or $C_3$–$C_7$ cycloalkyl, $C_6$–$C_{10}$ aryl or $C_7$–$C_{11}$ aralkyl radicals, wherein these various radicals are unsubstituted or substituted with one or more atoms or radicals selected from the group consisting of halogen atoms, $C_1$–$C_4$ alkyl radicals, mono- or polyhalo($C_1$–$C_4$ alkyl) radicals, $C_1$–$C_4$ alkoxy radicals and mono- or polyhalo ($C_1$–$C_4$ alkoxy) radicals; or the agriculturally acceptable salified forms of these compounds;

wherein said compound useful as an intermediate is selected from the group consisting of compounds of the formulae:

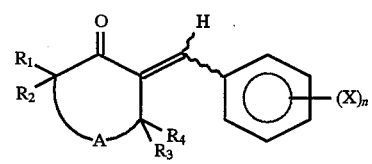

VII

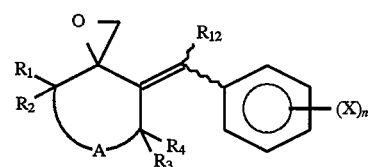

IX

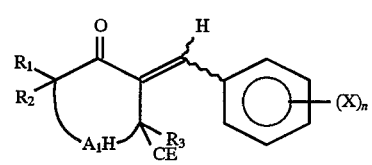

VIII

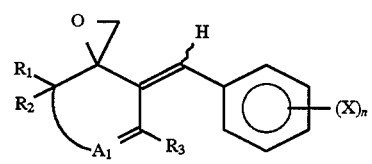

X in which the substituents in said compound useful as an intermediate are defined as follows:

A is —$CR_6R_7$— or —$CR_6R_7CR_8R_9$— or —$CR_6R_7CR_8R_9CR_{10}R_{11}$—;

$A_1$ is $CR_7$=, —$CR_6R_7$—$CR_9$= or —$CR_6R_7$—$CR_8R_9$—$CR_{11}$=;

X is a halogen atom, or a cyano or nitro group, or a $C_1$–$C_4$ alkyl or $C_1$–$C_4$ alkoxy group, which is unhalogenated or halogenated;

n is zero or a positive integer less than 6, wherein the groups X are identical or different when n is greater than 1;

$R_1$ and $R_2$ are each an unsubstituted $C_1$–$C_4$ alkyl radical;

$R_3$ and $R_6$ to $R_{11}$ which are identical or different, denote a hydrogen atom; a $C_1$–$C_4$ alkyl radical which is unsubstituted or substituted with one or more atoms or radicals selected from the group consisting of halogen atoms, $C_1$–$C_4$ alkoxy and mono- or polyhalo($C_1$–$C_4$ alkoxy) radicals; and $R_4$ and $R_{12}$ denote a hydrogen atom, a halogen atom, a $C_1$–$C_4$ alkyl radical, which is unsubstituted or substituted with one or more atoms or radicals selected from the group consisting of halogen atoms, $C_1$–$C_4$ alkoxy, mono- or polyhalo($C_1$–$C_4$ alkoxy), $C_2$–$C_4$ alkenyl, $C_2$–$C_4$ alkynyl, mono- or polyhalo($C_2$–$C_4$ alkenyl) and mono- or polyhalo($C_2$–$C_4$ alkynyl) radicals.

2. The compound useful as an intermediate in the preparation of a benzylidene)-azolylmethylcycloalkane or -alkene fungicide of claim 1 is 2,2-dimethyl-5-(4-chlorobenzylidene)-1-cyclopentanone.

3. The compound useful as an intermediate in the preparation of a benzylidene)-azolylmethylcycloalkane or -alkene fungicide of claim 1 is 7-(4-chlorobenzylidene)-4,4-dimethyl-1-oxaspiro heptane.

4. The compound useful as an intermediate in the preparation of a benzylidene)-azolylmethylcycloalkane or -alkene fungicide of claim 1 is 2,2-dimethyl-4-chloro-5-(4-chlorobenzylidene)-1-cyclopentanone.

5. The compound useful as an intermediate in the preparation of a benzylidene)-azolylmethylcycloalkane or -alkene fungicide of claim 1 is 2,2-dimethyl-5-chloro-6-(4-chlorobenzylidene)-1-cyclohexanone.

6. The compound useful as an intermediate in the preparation of a (benzylidene)-azolylmethylcycloalkane or -alkene fungicide of claim 1 is 2,2-dimethyl-6-(4-chlorobenzylidene)-1-cyclohexanone.

7. The compound useful as an intermediate in the preparation of a (benzylidene)-azolylmethylcycloalkane or -alkene fungicide of claim 1 is 2-(4-chlorobenzylidene)-6-methylcyclohexanone.

8. The compound useful as an intermediate in the preparation of a (benzylidene)azolylmethylcycloalkane or -alkene fungicide of claim 1 is 8-(4-chlorobenzylidene)-4,4-dimethyl-1-oxaspiro octane.

9. The compound useful as an intermediate of claim 1, wherein the substituents $R_1$ and $R_2$ are methyl and the substituent X is a halogen atom.

* * * * *